(12) United States Patent
Lindstedt-Alstermark et al.

(10) Patent No.: US 7,429,675 B2
(45) Date of Patent: Sep. 30, 2008

(54) PROCESS FOR THE PREPARATION OF RACEMIC 2-{[2-(4-HYDROXYPHENYL)ETHYL]THIO}-3-[4-(2-{4-[(METHYLSULFONYL)OXY]PHENOXY}ETHYL)PHENYL]-PROPANOIC ACID

(75) Inventors: Eva-Lotte Lindstedt-Alstermark, Mölndal (SE); Kjell Andersson, Mölndal (SE); Henrik Sorensen, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 35 days.

(21) Appl. No.: 10/561,161

(22) PCT Filed: Jun. 16, 2004

(86) PCT No.: PCT/GB2004/002599

§ 371 (c)(1), (2), (4) Date: Dec. 16, 2005

(87) PCT Pub. No.: WO2004/113285

PCT Pub. Date: Dec. 29, 2004

(65) Prior Publication Data

US 2006/0167309 A1    Jul. 27, 2006

(30) Foreign Application Priority Data

Jun. 19, 2003    (GB) ................... 0314260.1

(51) Int. Cl.
*C07B 55/00* (2006.01)
*C07F 7/02* (2006.01)
*C07F 7/04* (2006.01)
*C07C 303/00* (2006.01)

(52) U.S. Cl. .................. 562/401; 556/400; 556/427; 558/44

(58) Field of Classification Search ............ 558/44; 562/401; 556/400, 427
See application file for complete search history.

(56) References Cited

U.S. PATENT DOCUMENTS 4,918,196 A    4/1990    Doya et al. ............. 548/342

FOREIGN PATENT DOCUMENTS

| | | |
|---|---|---|
| JP | 61197530 | 9/1986 |
| WO | WO 95/21162 | 8/1995 |
| WO | WO 99/62871 | 12/1999 |
| WO | WO 99/62872 | 12/1999 |
| WO | WO 03/051826 | 6/2003 |

*Primary Examiner*—Jafar Parsa
(74) *Attorney, Agent, or Firm*—Morgan, Lewis & Bockius LLP

(57) ABSTRACT

The present invention provides a process for the preparation of substantially racemic 2-{[2-(4-hydroxyphenyl)ethyl]thio}-3-[4-(2-{4-[(methylsulfonyl)oxy]phenoxy}ethyl)phenyl]-propanoic acid which comprises reacting 2-{[2-(4-hydroxyphenyl)ethyl]thio}-3-[4-(2-{4-[(methylsulfonyl)oxy]phenoxy}ethyl)phenyl]propanoic acid enriched in one enantiomer with a base in an inert solvent.

7 Claims, No Drawings

PROCESS FOR THE PREPARATION OF RACEMIC 2-{[2-(4-HYDROXYPHENYL)ETHYL]THIO}-3-[4-(2-{4-[(METHYLSULFONYL)OXY] PHENOXY}ETHYL)PHENYL]-PROPANOIC ACID

FIELD OF THE INVENTION

The present invention relates to a process for the preparation of certain of 3-phenyl-2-arylalkylthiopropionic acid derivatives which have utility in treating clinical conditions including lipid disorders (dyslipidemias) whether or not associated with insulin resistance and other manifestations of the metabolic syndrome.

BACKGROUND OF THE INVENTION

Co-pending PCT application No. PCT/GB02/05743 discloses compounds of formula A

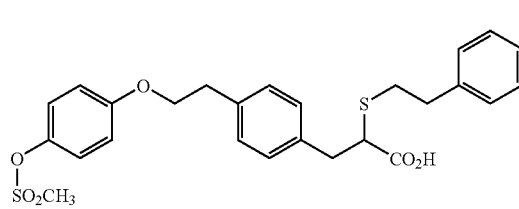

wherein $R^1$ represents chloro, fluoro or hydroxy as well as optical isomers and racemates thereof as well as pharmaceutically acceptable salts, prodrugs, solvates and crystalline forms thereof which are selective PPARα modulators. These compounds are useful in treating clinical conditions including lipid disorders (dyslipidemias) whether or not associated with insulin resistance and other manifestations of the metabolic syndrome. The above compounds contain a chiral centre. Often one enantiomer is much more active than the other and the preferred enantiomer is obtained by a resolution process or by chiral chromatography. By its nature a resolution process of a racemic mixture leads to 50% of the undesired material being discarded. The situation can be improved if the undesired enantiomer can be converted back into a racemic mixture by a racemisation process. Therefore there is a need for an efficient and cost effective process for racemising the undesired isomer so that the resolution step can be repeated and reduce the material wastage in the process.

DESCRIPTION OF THE INVENTION

The present invention provides a process for the preparation of substantially racemic 2-{[2-(4-hydroxyphenyl)ethyl]thio}-3-[4-(2-{4-[(methylsulfonyl)oxy]phenoxy}-ethyl)phenyl]-propanoic acid which comprises reacting 2-{[2-(4-hydroxyphenyl)ethyl]thio}-3-[4-(2-{4-[(methylsulfonyl)oxy]phenoxy}ethyl)phenyl]propanoic acid enriched in one enantiomer with a base in an inert solvent. Optionally the acid may be converted into an ester prior to racemisation or may converted into an ester during the racemisation. Suitable esters include $C_{1-6}$ alkyl esters for example the methyl and ethyl ester. Suitable bases include potassium hydroxide or sodium hydroxide. Suitably the racemised ester is then hydrolysed to give the racemic acid for example by base hydrolysis or by acid hydrolysis.

In one aspect the process comprises reacting 2-{[2-(4-hydroxyphenyl)ethyl]thio}-3-[4-(2-{4-[(methylsulfonyl)oxy]phenoxy}ethyl)phenyl]propanoic acid enriched in one enantiomer with a halosilane in the presence of a nitrogenous base in the presence of an inert solvent at a temperature in the range of 0 to 150° C.

The term enriched means that one enantiomer comprises >50%, preferably between 60 and 80% and most preferably between 80 and 100% of the 2-{[2-(4-hydroxyphenyl)-ethyl]thio}-3-[4-(2-{4-[(methylsulfonyl)oxy]phenoxy}ethyl)phenyl]propanoic acid in a mixture of the enantiomers of this acid.

In another aspect the present invention comprises reacting a compound of formula I

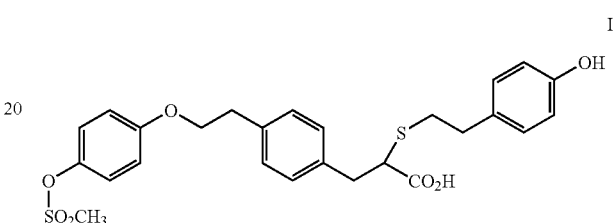

enriched in one enantiomer with a chlorosilane of formula $ClSiR^1R^2R^3$ in which $R^1$, $R^2$, and $R^3$ independently represent a $C_{1-6}$ alkyl group or aryl in the presence of a nitrogenous base in the presence of an inert solvent at a temperature in the range of 0 to 150° C. to give a compound of formula II

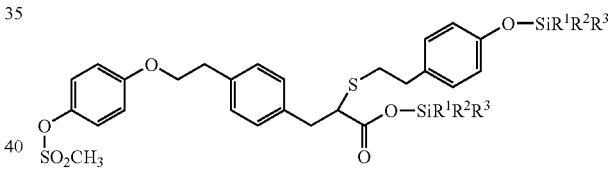

in which $R^1$, $R^2$, and $R^3$ are previously defined which is hydrolysed to give a racemic compound of formula III

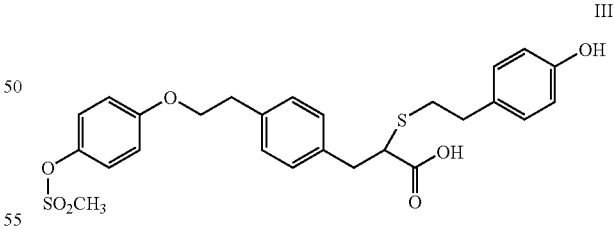

Suitable nitrogenous bases include 1,8 diazabicyclo[5.4.0] undec-7-ene, trialkylamines for example triethylamine, optionally substituted pyridines and optionally substituted imidazoles. Particularly the base is 1,8 diazabicyclo[5.4.0] undec-7-ene.

Suitable halosilanes include chlorotrialkyl silanes, for example chlorotriethylsilane and chlorodimethyltertbutylsilane and chlorotriarylsilanes for example chlorotriphenylsilane and mixed chloroarylalkyl silanes for example chlorodimethylphenyl silane. Particularly the chlorosilane is chlorotrimethylsilane.

In yet another aspect the present invention comprises reacting a compound of formula I

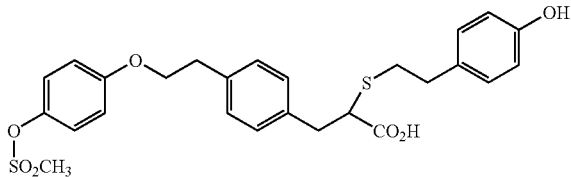

I enriched in one enantiomer with chlorotrimethylsilane in the presence of 1,8 diazabicyclo[5.4.0]undec-7-ene in the presence of an inert solvent at a temperature in the range of 0 to 150° C. to give a compound of formula IV

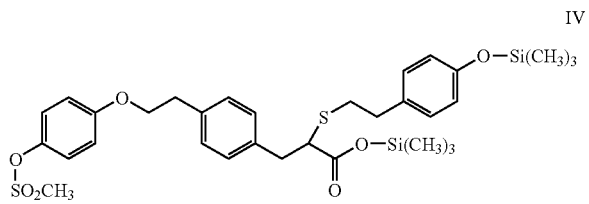

IV which is hydrolysed to give a racemic compound of formula III

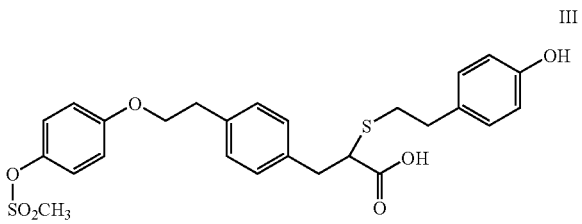

III

The compounds of the invention may be isolated from their reaction mixtures using conventional techniques. Hydrolysis is preferably carried out in the presence of an acid for example hydrochloric acid but basic hydrolysis may also be used.

The expression "inert solvent" refers to a solvent that does not react with the starting materials, reagents, intermediates or products in a manner that adversely affects the yield of the desired product. Suitable solvents include ethers, for example dialkyl ethers, especially di$C_{1-6}$ alkyl ethers, or cyclic ethers for example tetrahydrofuran or hydrocarbons for example toluene.

Aryl means phenyl or naphthyl, preferably phenyl, each of which is optionally substituted by one or more $C_{1-6}$ alkyl $C_{1-6}$ alkoxy or halo.

Preferably the enriched acid contains more of the (+)enantiomer (as measured in the conditions described below).

EXAMPLES $^1$H NMR and $^{13}$C NMR measurements were performed on a Varian Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale (δ).

Unless otherwise stated, chemical shifts are given in ppm with the solvent as internal standard.

ABBREVIATIONS

DMSO dimethyl sulfoxide
EtOAc ethyl acetate
DMF N,N-dimethylformamide
THF tetrahydrofuran
MeCN acetonitrile
MeOH methanol
TFA trifluoroacetic acid
NH$_4$OAc ammonium acetate
t triplet
s singlet
d doublet
q quartet
m multiplet
bs broad singlet Preparation of Staring Material 2-{[2-(4-Hydroxyphenyl)ethyl]thio}-3-[4-(2-{4-[(methylsulfonyl)oxy]phenoxy}-ethyl)phenyl]propanoic acid (i) Methyl 2-chloro-3-[4-(2-hydroxyethyl)phenyl]propanoate 2-(4-Aminophenyl)ethanol (11 g, 81 mmol) and 32 ml conc HCl was dissolved in acetone and cooled to 0° C. Sodium nitrite (5.6 g, 81 mmol) in 20 ml water was added dropwise. The temperature was kept under 0° C. After one hour, methyl acrylate (70 g, 808 mmol) and CuI (1.6 g, 8 mmol) were added (<0° C.). The reaction mixture was stirred at room temperature overnight. The solvent was evaporated and water was added. The water phase was extracted three times with EtOAc, the organic phases were pooled and washed with water, dried (MgSO$_4$) and evaporated under reduced pressure. The crude product was purified by flash chromatography using a 65:35 mixture of EtOAc and heptane as eluent. Further purification by preparative HPLC (using a gradient of CH$_3$CN/5% CH$_3$CN-waterphase containing 0.1M NH$_4$OAc as eluent) gave 9.7 g product (yield 49%) as an oil.

$^1$HNMR (400 MHz, CDCl$_3$): 2.84 (t, 3H), 3.15 (dd, 1H), 3.35 (dd, 1H), 3.75 (s, 3H), 3.84 (t, 3H), 4.43 (t, 1H), 7.17 (d, 4H)

(ii) Methyl 3-(4-{2-[4-(benzyloxy)phenoxy]ethyl}phenyl)-2-chloropropanoate

Triphenylphosphine (2.4 g, 9 mmol) was added to a solution of methyl 2-chloro-3-[4-(2-hydroxyethyl)phenyl]propanoate (2.1 g, 8.5 mmol) and 4-(benzyloxy)phenol (1.7 g, 8 mmol) in 20 ml toluene under nitrogen atmosphere. The solution was warmed to 55° C. and diisopropyl azodicarboxylate (1.8 g, 9 mmol) was added. The reaction mixture was stirred at 55° C. overnight. The mixture was allowed to cool and the solvent was evaporated under reduced pressure. The crude product was purified by flash chromatography using a 80:20 mixture of heptane and EtOAc as eluent to yield 2.28 g of the desired product (yield 61%) as colourless crystals.

¹HNMR (400 MHz, CDCl₃): 3.05 (t, 2H), 3.16 (dd, 1H), 3.36 (dd, 1H), 3.75 (s, 3H), 4.12 (t, 2H), 4.45 (t, 1H), 5.01 (s, 2H), 6.82 (m, 2H), 6.90 (m, 2H), 7.13-7.27 (m, 4H), 7.29-7.47 (m, 5H).

(iii) Methyl 2-chloro-3-{4-[2-(4-hydroxyphenoxy)ethyl]phenyl}propanoate

Methyl 3-(4-{2-[4-(benzyloxy)phenoxy]ethyl}phenyl)-2-chloropropanoate (1.0 g, 2.4 mmol) and dimethyl sulfide (0.9 g, 14 mmol) was dissolved in 60 ml CH₂Cl₂. Boron trifluoride etherate (2.0 g, 14 mmol) was added dropwise to the stirred solution. The reaction mixture was stirrred for two days at room temperature. Another equivalent (0.4 g, 2.87 mmol) boron trifluoride etherate was added and the stirring was continued overnight.

Water was added. The phases were separated and the aqueous phase was extracted twice with CH₂Cl₂. The organic phases were pooled, washed (water, brine), dried (Na₂SO₄) and evaporated under reduced pressure. Futher purification by preparative HPLC using a gradient of CH₃CN/5% CH₃CN-waterphase containing 0.1M NH₄OAc gave 0.55 g of the desired product (yield 52%) as an oil.

¹HNMR (400 MHz, CDCl₃): 3.04 (t, 2H), 3.16 (dd, 1H), 3.35 (dd, 1H), 3.75 (s, 3H), 4.10 (t, 2H), 4.40 (t, 1H), 6.75 (m, 4H), 7.12-7.29 (m, 4H).

(iv) Methyl 2-chloro-3-[4-(2-{4-[(methylsulfonyl)oxy]phenoxy}ethyl)phenyl]propanoate Methyl 2-chloro-3-{4-[2-(4-hydroxyphenoxy)ethyl]phenyl}propanoate (334 mg, 1.0 mmol) and triethylamine (303 mg, 3.0 mmol) was dissolved in 20 ml dichlormethane and cooled to −20° C. under nitrogen atmosphere. Methanesulfonyl chloride (114 mg, 1.0 mmol) was added dropwise. The mixture was allowed to reach room temperature. After 2 hours dichlormethane was added, the mixture was washed (water, brine), dried (Na₂SO₄) and evaporated under reduced pressure to yield 394 mg pure product (yield 96%).

¹HNMR (400 MHz, CDCl₃): 3.02-3.11 (m, 5H), 3.15 (dd, 1H), 3.35 (dd, 1H), 3.74 (s, 3H), 4.14 (t, 2H), 4.44 (t, 1H), 5.29 (s, 2H), 6.88 (d, 2H), 7.14-7.25 (m, 6H).

(v) Methyl 2-({2-[4-(benzyloxy)phenyl]ethyl}thio)-3-[4-(2-{4-[(methylsulfonyl)oxy]-phenoxy}ethyl)phenyl]propanoate 2-[4-(Benzyloxy)phenyl]ethanethiol (334 mg, 1.4 mmol), methyl 2-chloro-3-[4-(2-{4-[(methylsulfonyl)oxy]phenoxy}ethyl)phenyl]propanoate (394 mg, 0.95 mmol) and potassium carbonate (189 mg, 1.4 mmol) were dissolved in 14 ml dry DMF and stirred under nitrogen atmosphere at room temperature overnight. The solvent was evaporated under reduced pressure and the residue was dissolved in toluene. The organic phase was washed (water, brine), dried (MgSO₄) and evaporated. Futher purification by preparative HPLC using a gradient of CH₃CN/5% CH₃CN-waterphase containing 0.1M NH₄OAc gave 477 mg of the desired product (yield 75%).

¹HNMR (400 MHz, CDCl₃): 2.76-2.89 (m, 4H), 2.95 (dd, 1H), 3.09 (m, 5H), 3.20 (dd, 1H), 3.53 (m, 1H), 3.70 (s, 3H), 4.15 (t, 2H), 5.06 (s, 2H), 6.91 (m, 4H), 7.07-7.24 (m, 8H), 7.31-7.48 (m, 5H).

(vi) Methyl 2-{[2-(4-hydroxyphenyl)ethyl]thio}-3-[4-(2-{4-[(methylsulfonyl)oxy]-phenoxy}ethyl)phenyl]propanoate To a solution of methyl 2-({2-[4-(benzyloxy)phenyl]ethyl}thio)-3-[4-(2-{4-[(methylsulfonyl)oxy]phenoxy}ethyl)phenyl]propanoate (477 mg, 0.8 mmol) and 15 ml dichlormethane, dimethyl sulfide (239 mg, 3.8 mol) and boron trifluoride etherate (545 mg, 3.8 mmol) were added. After 18 hours of stirring water was added to the reaction. The phases were separated and the aqueous phase was extracted twice with dichlormethane. The organic phases were pooled, dried (MgSO₄) and evaporated under reduced pressure.

274 mg of the desired product (yield 67%) was obtained as an oil.

¹HNMR (400 MHz, CDCl₃): 2.70-2.85 (m, 4H), 2.91 (dd, 1H), 3.05 (t, 2H), 3.10 (s, 3H), 3.17 (dd, 1H), 3.49 (m, 1H), 3.68 (s, 3H), 4.13 (t, 2H), 6.72 (d, 2H), 6.87 (d, 2H), 6.99 (d, 2H), 7.10-7.22 (m, 6H)

(vii) 2-{[2-(4-Hydroxyphenyl)ethyl]thio}-3-[4-(2-{4-[(methylsulfonyl)oxy]-phenoxy}ethyl)phenyl]propanoic acid Methyl 2-{[2-(4-hydroxyphenyl)ethyl]thio}-3-[4-(2-{4-[(methylsulfonyl)oxy]phenoxy}-ethyl)phenyl]propanoate (105 mg, 0.2 mmol) was dissolved in 6.5 ml of a 7:1 mixture of THF and water and cooled on an ice-bath Lithium hydroxide (9.4 mg, 0.4 mmol) was added. Water was added to the reaction mixture after 24 hours of stirring at room temperature. The THF was evaporated under reduced pressure and the residue was acidified with 1M hydrochloric acid. The water phase was extracted with EtOAc (×3), the organic phases were pooled, washed (water, brine), dried (MgSO₄) and evaporated. The crude product was purified using preparative HPLC (eluent: CH₃CN/5% CH₃CN-waterphase containing 0.1M NH₄OAc) to give 74 mg of the desired product (yield 97%) as an oil.

¹HNMR (400 MHz, CDCl₃): 2.68-2.95 (m, 5H), 3.05 (t, 2H), 3.10 (s, 3H), 3.17 (dd, 1H), 3.47 (m, 1H), 4.12 (t, 2H), 6.70 (d, 2H), 6.86 (d, 2H), 6.97 (d, 2H), 7.12-7.21 (m, 6H). ¹³CNMR (100 MHz, CDCl₃): 33.8, 35.1, 35.5, 37.2, 37.3, 48.1, 69.3, 115.6, 115.8, 123.3, 129.3, 129.4, 129.9, 132.3, 136.2, 136.9, 142.8, 154.4, 158.0, 177.2.

(viii) (−)-2-{[2-(4-hydroxyphenyl)ethyl]thio}-3-[4-(2-{4-[(methylsulfonyl)oxy]phenoxy}-ethyl)phenyl]propanoic acid The racemate of 2-{[2-(4-hydroxyphenyl)ethyl]thio}-3-[4-(2-{4-[(methylsulfonyl)-oxy]phenoxy}ethyl)phenyl]propanoic acid was separated into its enantiomers using chiral chromatography. A Chiralpak AD JDB01+ AS003 (336×100 mm i.d.) and ethanol/formic acid 100/0.01% was used as mobile phase. The racemate (9 g) was dissolved in ethanol and injected onto the column. The first eluting peak was collected and UV-detected. The product (4.1 g) was obtained with an enantiomeric purity >99%. The optical rotation was found to be $[\alpha]^{20}_D = -33°$ by dissolving the enantiomer in methanol to give a concentration of 0.64 g/100 ml. The optical rotation was measured at 20° C. using the sodium line at 589 nm. The (+) enantiomer is isolated subsequently from the column and is used as a starting material for the racemisation reaction.

¹H NMR (500 MHz, CD₃OD): 7.17-7.22 (6H, m), 6.99 (2H, d), 6.94 (2H, d), 6.69 (2H, d), 4.17 (2H, t), 3.46 (1H, t), 3.16 (3H, s), 3.13 (1H, dd), 3.05 (2H, t), 2.69-2.88 (5H, m).

Example 1

1,8 Diazabicyclo[5.4.0]undec-7-ene (DBU) (4.11 g) was added by syringe over 5 minutes to a stirred mixture of (+)-2-{[2-(4-hydroxyphenyl)ethyl]thio}-3-[4-(2-{4-[(methyl-sulfonyl)oxy]phenoxy}ethyl)-phenyl]propanoic acid (3.83 g), toluene (8.65 g) and tetrahydrofuran (44 g) followed by the addition of chlorotrimethylsilane (2.24 g) by syringe over 5 minutes. The resultant slurry was stirred at room temperature until the reaction was complete (3 hours). 2N Hydrochloric acid (31.2 g) was added to the reaction mixture to hydrolyse the TMS ester, followed by brine. After separation of the aqueous layer, further brine was added, and the pH was adjusted to pH 2.5-3.5 by the addition of 1M sodium bicarbonate solution. The aqueous layer was separated and the organic layer was distilled at atmospheric pressure to remove water. Ethanol was added and a vacuum distillation carried out to remove THF and give a solution of racemic 2-{[2-(4-hydroxyphenyl)ethyl]thio}-3-[4-(2-{4-[(methylsulfonyl)oxy]-phenoxy}ethyl)phenyl]-propanoic acid in ethanol.

What is claimed is:

1. A process for the preparation of substantially racemic 2-{[2-(4-hydroxyphenyl)ethyl]thio}-3-[4-(2-{4-[(methyl-sulfonyl)oxy]phenoxy}ethyl)-phenyl]propanoic acid comprising reacting a compound of formula I

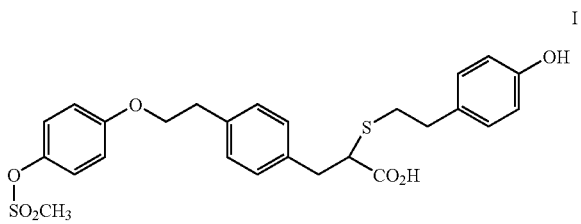

enriched in one enantiomer with a chlorosilane of formula ClSiR$^1$R$^2$R$^3$ in which R$^1$, R$^2$, and R$^3$ independently represent a C$_{1-6}$ alkyl group or aryl in the presence of a nitrogenous base in the presence of an inert solvent at a temperature in the range of 0 to 150° C. to give a compound of formula II

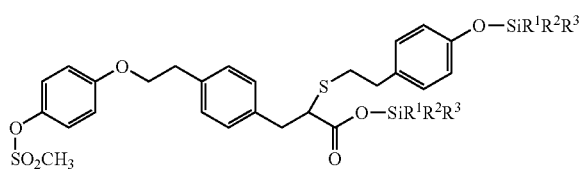

in which R, R$^2$, and R$^3$ are previously defined which is hydrolysed to give a racemic compound of formula III

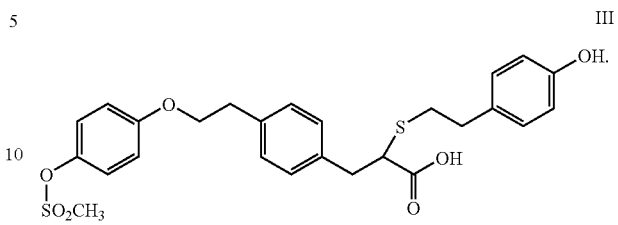

2. A compound of formula II

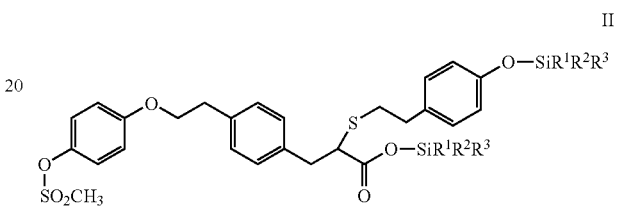

wherein R$^1$, R$^2$, and R$^3$ independently represent a C$_{1-6}$ alkyl group or aryl.

3. A compound of formula IV

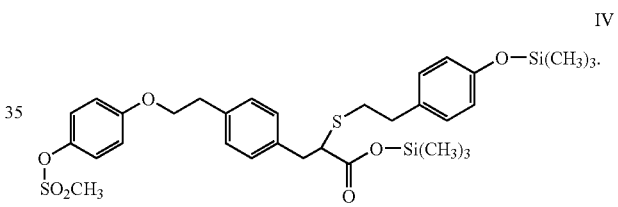

4. A process according to claim 1 wherein the chlorosilane is selected from: chlorotriethylsilane, chlorodimethyltertbutylsilane, chlorotriphenylsilane and chlorodimethylphenyl silane.

5. A process according to claim 1 wherein the chlorosilane is chlorotrimethylsilane.

6. A process according to claim 1 wherein the nitrogenous base is selected from 1,8 diazabicyclo[5.4.0]undec-7-ene, a trialkylamine, an optionally substituted pyridine or an optionally substituted imidazole.

7. A process according to claim 6 wherein the nitrogenous base is 1,8 diazabicyclo[5.4.0]undec-7-ene.

* * * * *